US008753501B2

(12) United States Patent
Zimmerman et al.

(10) Patent No.: US 8,753,501 B2
(45) Date of Patent: Jun. 17, 2014

(54) PROCESS AND APPARATUS FOR PRODUCING DIESEL

(75) Inventors: Paul R. Zimmerman, Palatine, IL (US); Andrew P. Wieber, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 171 days.

(21) Appl. No.: 13/324,186

(22) Filed: Dec. 13, 2011

(65) Prior Publication Data
US 2013/0098803 A1    Apr. 25, 2013

Related U.S. Application Data (60) Provisional application No. 61/549,978, filed on Oct. 21, 2011.

(51) Int. Cl.
| $C10G\ 65/12$ | (2006.01) |
| $C10G\ 65/00$ | (2006.01) |
| $C10G\ 65/02$ | (2006.01) |
| $C10G\ 45/02$ | (2006.01) |

(52) U.S. Cl.
CPC ............ C10G 65/12 (2013.01); C10G 2400/04 (2013.01); C10G 2300/202 (2013.01)
USPC ............... 208/58; 208/49; 208/106; 208/209; 208/216 R (58) Field of Classification Search
USPC ........... 208/46, 49, 58, 60, 78, 79, 80, 81, 83, 208/106, 145, 208 R, 209, 216 R, 309, 361
See application file for complete search history.

(56) References Cited

U.S. PATENT DOCUMENTS

| 3,592,757 A | 7/1971 | Baral |
| 3,598,722 A | 8/1971 | Carson |
| 3,607,726 A | 9/1971 | Hallman |
| 3,623,974 A | 11/1971 | Mounce et al. |
| 3,655,551 A | 4/1972 | Hass et al. |
| 4,211,634 A | 7/1980 | Bertolacini et al. |
| 4,212,729 A | 7/1980 | Hensley, Jr. et al. |
| 5,403,469 A | 4/1995 | Vauk et al. |
| 5,447,621 A | 9/1995 | Hunter |
| 5,453,177 A | 9/1995 | Goebel et al. |

(Continued)

FOREIGN PATENT DOCUMENTS

| EP | 0665283 A2 | 8/1995 |
| WO | 2009008878 A1 | 1/2009 |
| WO | 2009008879 A1 | 1/2009 |

OTHER PUBLICATIONS

Bhaskar, "Mild hydrocracking of FCC feeds yields more fuels, boosts margins", Oil & Gas Journal, Jun. 10, 2002, pp. 62-65.

(Continued)

Primary Examiner — Walter D Griffin
Assistant Examiner — Derek Mueller
(74) Attorney, Agent, or Firm — James C Paschall (57) ABSTRACT

A process and apparatus are disclosed for hydrocracking hydrocarbon feed in a hydrocracking unit and hydrotreating a diesel product from the hydrocracking unit in a hydrotreating unit. The hydrocracking unit and the hydrotreating unit share the same recycle gas compressor. A make-up hydrogen stream may also be compressed in the recycle gas compressor. A warm separator separates recycle gas and hydrocarbons from diesel in the hydrotreating effluent, so fraction of the diesel is relatively simple. The warm separator also keeps the diesel product separate from the more sulfurous diesel in the hydrocracking effluent, and still retains heat needed for fractionation of lighter components from the low sulfur diesel product.

12 Claims, 2 Drawing Sheets

(56) References Cited

U.S. PATENT DOCUMENTS

| | | | |
|---|---|---|---|
| 5,968,346 | A | 10/1999 | Jung et al. |
| 6,123,830 | A | 9/2000 | Gupta et al. |
| 6,149,800 | A | 11/2000 | Iaccino et al. |
| 6,200,462 | B1 | 3/2001 | Cash et al. |
| 6,217,746 | B1 | 4/2001 | Thakkar et al. |
| 6,294,080 | B1 | 9/2001 | Thakkar et al. |
| 6,315,889 | B1 | 11/2001 | Thakkar et al. |
| 6,444,116 | B1 | 9/2002 | Galiasso et al. |
| 6,656,348 | B2 | 12/2003 | Dassori et al. |
| 6,676,828 | B1 | 1/2004 | Galiasso et al. |
| 6,740,226 | B2 | 5/2004 | Mehra et al. |
| 6,843,906 | B1 | 1/2005 | Eng |
| 7,074,321 | B1 | 7/2006 | Kalnes |
| 7,087,153 | B1 | 8/2006 | Kalnes |
| 7,097,760 | B1 | 8/2006 | Kalnes et al. |
| 7,238,275 | B2 | 7/2007 | Stupin et al. |
| 7,238,276 | B2 | 7/2007 | Fang et al. |
| 7,238,277 | B2 | 7/2007 | Dahlberg et al. |
| 7,271,303 | B1 | 9/2007 | Sechrist et al. |
| 7,470,358 | B1 | 12/2008 | Kalnes |
| 7,507,325 | B2 | 3/2009 | Gueret et al. |
| 7,531,082 | B2 | 5/2009 | Mukherjee et al. |
| 7,547,386 | B1 | 6/2009 | Thakkar et al. |
| 7,686,941 | B2 | 3/2010 | Brierley et al. |
| 7,790,020 | B2 | 9/2010 | Kokayeff et al. |
| 7,794,588 | B2 | 9/2010 | Kokayeff et al. |
| 7,815,791 | B2 | 10/2010 | Keusenkothen |
| 7,837,860 | B1 | 11/2010 | Hoehn et al. |
| 2003/0089638 | A1 | 5/2003 | Gueret et al. |
| 2007/0017851 | A1 | 1/2007 | Mehra et al. |
| 2008/0159928 | A1 | 7/2008 | Kokayeff et al. |
| 2009/0095655 | A1 | 4/2009 | Kokayeff et al. |
| 2009/0313890 | A1 | 12/2009 | Lopez et al. |
| 2009/0321310 | A1 | 12/2009 | Kokayeff et al. |
| 2009/0321319 | A1 | 12/2009 | Kokayeff et al. |
| 2010/0043279 | A1 | 2/2010 | Abhari et al. |
| 2010/0160699 | A1 | 6/2010 | Frey et al. |
| 2010/0200458 | A1 | 8/2010 | Kalnes |

OTHER PUBLICATIONS

Bollinger, "Gas Processing Techniques: Optimizing Hydrocracker Hydrogen", Chem. Eng. Prog., May 1984, pp. 51-57.
Kimbrell, "Hydrogen Processing—General Process", 1996 NPRA Conference Question and Answer Session on Refining and Petrochemical Technology, pp. 150-151.
Putek, "Upgrade hydrocracked resid through integrated hydrotreating", Hydrocarbon Processing, Sep. 2008, pp. 83-92.
Turner, "Consider revamping hydrotreaters to handle higher H2 partial pressures", Hydrocarbon Processing, Mar. 2004, pp. 61-70.
Zhu, "Application of high pressure hot separation schemes in hydrocrackers", Petroleum Refinery Engineering, Sep. 1995, v25, n5, p. 1-5. (full Chinese to English translation).
U.S. Appl. No. 13/076,647, filed Mar. 31, 2011, Wieber.
U.S. Appl. No. 13/076,658, filed Mar. 31, 2011, Wieber.
U.S. Appl. No. 13/076,670, filed Mar. 31, 2011, Wieber.
U.S. Appl. No. 13/076,680, filed Mar. 31, 2011, Wieber.
U.S. Appl. No. 13/076,608, filed Mar. 31, 2011, Wieber.
U.S. Appl. No. 13/076,631, filed Mar. 31, 2011, Wieber.
U.S. Appl. No. 13/167,945, filed Jun. 24, 2011, Wieber.
U.S. Appl. No. 13/167,979, filed Jun. 24, 2011, Wieber.
U.S. Appl. No. 13/168,052, filed Jun. 24, 2011, Wieber.
U.S. Appl. No. 13/168,078, filed Jun. 24, 2011, Wieber.
U.S. Appl. No. 13/324,209, filed Dec. 13, 2011, Zimmerman.
U.S. Appl. No. 13/324,209, filed Dec. 13, 2011, Zimmerman et al.
Parkash, Refining Processes Handbook, 2003, Elsevier, pp. 47 & 76.

PROCESS AND APPARATUS FOR PRODUCING DIESEL

CROSS-REFERENCE TO RELATED APPLICATION

This application claims priority from Provisional Application No. 61/549,978 filed Oct. 21, 2011, the contents of which are hereby incorporated by reference.

FIELD OF THE INVENTION

The field of the invention is the production of diesel by hydrocracking

BACKGROUND OF THE INVENTION

Hydrocracking refers to a process in which hydrocarbons crack in the presence of hydrogen and catalyst to lower molecular weight hydrocarbons. Depending on the desired output, the hydrocracking zone may contain one or more beds of the same or different catalyst. Hydrocracking is a process used to crack hydrocarbon feeds such as vacuum gas oil (VGO) to diesel including kerosene and gasoline motor fuels.

Mild hydrocracking is generally used upstream of a fluid catalytic cracking (FCC) or other process unit to improve the quality of an unconverted oil that can be fed to the downstream unit, while converting part of the feed to lighter products such as diesel. As world demand for diesel motor fuel is growing relative to gasoline motor fuel, mild hydrocracking is being considered for biasing the product slate in favor of diesel at the expense of gasoline. Mild hydrocracking may be operated with less severity than partial or full conversion hydrocracking to balance production of diesel with the FCC unit, which primarily is used to make naphtha. Partial or full conversion hydrocracking is used to produce diesel with less yield of the unconverted oil which can be fed to a downstream unit.

Due to environmental concerns and newly enacted rules and regulations, saleable diesel must meet lower and lower limits on contaminates, such as sulfur and nitrogen. New regulations require essentially complete removal of sulfur from diesel. For example, the ultra low sulfur diesel (ULSD) requirement is typically less than about 10 wppm sulfur.

There is a continuing need, therefore, for improved methods of producing more diesel from hydrocarbon feedstocks than gasoline. Such methods must ensure that the diesel product meets increasingly stringent product requirements.

BRIEF SUMMARY OF THE INVENTION

In a process embodiment, the invention comprises a process for producing diesel from a hydrocarbon stream comprising compressing a make-up hydrogen stream in a compressor to provide a compressed make-up hydrogen stream. The compressed make-up hydrogen stream is further compressed in a recycle gas compressor to provide a compressed hydrogen stream. A hydrocracking hydrogen stream is taken from the compressed hydrogen stream. The hydrocarbon stream is hydrocracked in the presence of the hydrocracking hydrogen stream and hydrocracking catalyst to provide a hydrocracking effluent stream. At least a portion of the hydrocracking effluent stream is fractionated to provide a diesel stream. The diesel stream is hydrotreated in the presence of a hydrotreating hydrogen stream and hydrotreating catalyst to provide a hydrotreating effluent stream.

In an additional process embodiment, the invention further comprises a process for producing diesel from a hydrocarbon stream comprising compressing a make-up hydrogen stream in a compressor to provide a compressed make-up hydrogen stream. The hydrocarbon stream is hydrocracked in the presence of a hydrocracking hydrogen stream and hydrocracking catalyst to provide a hydrocracking effluent stream. The hydrocracking effluent stream is separated into a vaporous hydrocracking effluent stream comprising hydrogen and a liquid hydrocracking effluent stream. The vaporous hydrocracking effluent stream and the compressed make-up hydrogen stream are compressed to provide a compressed hydrogen stream. The hydrocracking hydrogen stream and a hydrotreating hydrogen stream are taken from the compressed hydrogen stream. The liquid hydrocracking effluent stream is fractionated to provide a diesel stream. The diesel stream is hydrotreated in the presence of the hydrotreating hydrogen stream and a hydrotreating catalyst to provide a hydrotreating effluent stream.

In an alternative additional process embodiment, the invention further comprises a process for producing diesel from a hydrocarbon stream comprising compressing a make-up hydrogen stream in a compressor to provide a compressed make-up hydrogen stream. The compressed make-up hydrogen stream is compressed in a recycle gas compressor to provide a compressed hydrogen stream. A hydrocracking hydrogen stream is taken from the compressed hydrogen stream. The hydrocarbon stream is hydrocracked in the presence of the hydrocracking hydrogen stream and hydrocracking catalyst to provide a hydrocracking effluent stream. At least a portion of the hydrocracking effluent stream is fractionated to provide a diesel stream. The diesel stream is hydrotreated in the presence of a hydrotreating hydrogen stream and hydrotreating catalyst to provide a hydrotreating effluent stream. Lastly, at least a portion of the hydrotreating effluent stream comprising hydrogen is mixed with at least a portion of the hydrocracking effluent stream.

In an apparatus embodiment, the invention further comprises an apparatus for producing diesel comprising a hydrocracking reactor in communication with a compressor on a make-up hydrogen line and a hydrocarbon feed line for hydrocracking the hydrocarbon stream to lower boiling hydrocarbons. A recycle gas compressor is in communication with the hydrocracking reactor and the make-up hydrogen line for compressing a vaporous hydrocracking effluent stream comprising hydrogen and a compressed make-up hydrogen stream to provide a compressed hydrogen stream in a compressed hydrogen line. Lastly, a hydrotreating reactor is in communication with the compressed hydrogen line and the hydrocracking reactor for hydrotreating a diesel stream to produce low sulfur diesel.

In an alternative apparatus embodiment, the invention further comprises an apparatus for producing diesel comprising a make-up hydrogen line. One or more compressors is in communication with the make-up hydrogen line for compressing the make-up hydrogen stream. A hydrocarbon feed line is for carrying a hydrocarbon stream. A hydrocracking reactor is in communication with the make-up hydrogen line and the hydrocarbon feed line for hydrocracking the hydrocarbon stream to lower boiling hydrocarbons. A recycle gas compressor is in communication with the hydrocracking reactor and the one or more compressors for compressing a vaporous hydrocracking effluent stream comprising hydrogen and a compressed make-up hydrogen stream to provide a compressed hydrogen stream in a compressed hydrogen line. A fractionation section is in communication with the hydrocracking reactor for fractionating a liquid hydrocracking effluent stream to produce a diesel stream carried in a diesel line. Lastly, a hydrotreating reactor is in communication with the compressed hydrogen line and the diesel line for hydrotreating the diesel stream to produce low sulfur diesel.

In a further apparatus embodiment, the invention further comprises an apparatus for producing diesel comprising a hydrocracking reactor in communication with one or more compressors on a make-up hydrogen line and a hydrocarbon feed line for hydrocracking the hydrocarbon stream to lower boiling hydrocarbons. A recycle gas compressor is in communication with the make-up hydrogen line and the hydrocracking reactor for compressing a vaporous hydrocracking effluent stream comprising hydrogen to provide a compressed hydrogen stream in a compressed hydrogen line. A hydrotreating reactor is in communication with the compressed hydrogen line and the hydrocracking reactor for hydrotreating the diesel stream to produce low sulfur diesel. A warm separator is in communication with the hydrotreating reactor for separating the hydrotreating effluent stream into a vaporous hydrotreating effluent stream comprising hydrogen in an overhead line and a liquid hydrotreating effluent stream in a bottoms line. Lastly, the recycle gas compressor is in communication with the overhead line.

DEFINITIONS

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of the reflux or reboil to the column.

As used herein, the term "True Boiling Point" (TBP) means a test method for determining the boiling point of a material which corresponds to ASTM D2892 for the production of a liquefied gas, distillate fractions, and residuum of standardized quality on which analytical data can be obtained, and the determination of yields of the above fractions by both mass and volume from which a graph of temperature versus mass % distilled is produced using fifteen theoretical plates in a column with a 5:1 reflux ratio.

As used herein, the term "conversion" means conversion of feed to material that boils at or below the diesel boiling range.

The cut point of the diesel boiling range is between about 343° and about 399° C. (650° to 750° F.) using the True Boiling Point distillation method.

As used herein, the term "diesel boiling range" means hydrocarbons boiling in the range of between about 132° and about 399° C. (270° to 750° F.) using the True Boiling Point distillation method.

DETAILED DESCRIPTION

Mild hydrocracking reactors operate at low severity and therefore low conversion. The diesel produced from mild hydrocracking is not of sufficient quality to meet applicable fuel specifications particularly with regard to sulfur. As a result, the diesel produced from mild hydrocracking must be processed in a hydrotreating unit to allow blending into finished diesel. In many cases, it is attractive to integrate the mild hydrocracking unit and the hydrotreating unit to reduce capital and operating costs.

A typical hydrocracking unit has both a cold separator and a cold flash drum. It often, but not always, has a hot separator and a hot flash drum. A typical hydrotreating unit has only a cold separator. The cold separator may be operated at a lower temperature for obtaining optimal hydrogen separation for use as recycle gas, but this proves thermally inefficient as the hydrotreated liquid stream must be reheated for fractionation to obtain the low sulfur diesel.

To avoid this cooling and reheating without impacting the hydrogen separation, a hydrotreating unit is utilized in parallel with hydrocracking unit, a common recycle gas compressor and a cold separator. The recycle gas splits to each unit after compression. Make-up gas can be added to the recycle gas stream upstream to the recycle gas compressor. Make-up gas may be added upstream of the recycle gas compressor, to utilize the recycle gas compressor for compression of hydrogen gas fed to the hydrocracking reactor and the hydrotreating reactor.

The hydrotreating unit may employ a warm separator to extract a warm liquid product and then combine the vaporous hydrotreating effluent phase with the hydrocracking effluent. This arrangement allows the hydrotreating and hydrocracking units to operate at similar pressures. Additionally, the vaporous hydrotreating effluent may be sent to the cold separator to further separate hydrogen from hydrocarbon to provide recycle gas. The liquid hydrotreating effluent from the warm separator does not have to be reheated as much before fractionation. Furthermore, the liquid hydrotreating effluent comprises predominantly low sulfur diesel, so fractionation of the low sulfur diesel is simpler.

The invention involves splitting all make-up gas and recycle gas between the hydrocracking unit and the hydrotreating unit. The make-up gas addition to the hydrocracking unit is advantageous because the feedstock to the hydrocracking reactor will typically have high coke precursors which lead to higher catalyst deactivation rates and shorter catalyst life. Using the make-up gas to increase the hydrogen partial pressure in the hydrocracking reactor will render the hydrocracking operation more efficient.

The apparatus and process 8 for producing diesel comprise a compression section 10, a hydrocracking unit 12, a hydrotreating unit 14 and a fractionation zone 16. Hydrocarbon feed is first fed to the hydrocracking unit 12 and converted to lower boiling hydrocarbons including diesel. The diesel is fractionated in a fractionation section therein and forwarded to the hydrotreating unit 14 to provide lower sulfur diesel.

A make-up hydrogen stream in a make-up hydrogen line 20 is fed to a train of one or more compressors 22 in the compression section 10 to boost the pressure of the make-up hydrogen stream and provide a compressed make-up stream in line 26. The compressed make-up stream in compressed make-up hydrogen line 26 may join with a vaporous hydrocracking effluent stream comprising hydrogen in an overhead line 42 to provide an introductory hydrogen stream in line 28. The compressed make-up hydrogen stream may be added to the vaporous hydrocracking effluent stream upstream of a recycle gas compressor 50 at a location such that, relative to the compressed make-up hydrogen line 26, the recycle gas compressor 50 is upstream of any hydroprocessing reactor, such as a hydrocracking reactor 36 or a hydrotreating reactor 92. Consequently, no hydroprocessing reactor is located intermediate of the compressed make-up hydrogen line 26 and the recycle gas compressor 50.

The introductory hydrogen stream in line 28 comprising the compressed make-up hydrogen stream and the vaporous hydrocracking effluent stream may be compressed in a recycle gas compressor 50 to provide a compressed hydrogen stream in a compressed hydrogen line 52 which includes compressed vaporous hydrocracking effluent. The recycle gas compressor 50 may be in downstream communication with the hydrocracking reactor 36, the make-up hydrogen line 20 and the one or more compressors 22.

In an embodiment, the compressed make-up hydrogen stream may be added to the compressed hydrogen line 52 downstream of the recycle gas compressor 50. However, the pressure of the compressed hydrogen stream in line 52 may be too great to admit the make-up hydrogen stream without adding more compressors on the make-up hydrogen line 20. Consequently, adding the compressed make-up hydrogen stream to the vaporous hydrocracking effluent stream in line 42 upstream of the recycle gas compressor 50 may be advantageous, despite the increased duty on the recycle gas compressor 50 due to greater throughput. Adding the compressed make-up hydrogen stream upstream of the recycle gas compressor 50, however, may diminish the need for an additional compressor 22 on the make-up hydrogen line 20.

The compressed hydrogen stream in line 52 may be split between two hydrogen streams at a split 54. A first hydrocracking hydrogen stream is taken from the compressed hydrogen stream in the compressed hydrogen line 52 at the split 54 in a first hydrogen split line 30. A second hydrotreating hydrogen stream is taken from the compressed hydrogen stream in the compressed hydrogen line 52 at the split 54 in a second hydrogen split line 56. The first hydrogen split line 30 is in upstream communication with the hydrocracking reactor 36 and the second hydrotreating hydrogen stream in a second hydrogen split line 56 is in upstream communication with the hydrotreating reactor 92.

The hydrocracking hydrogen stream in the first hydrogen split line 30 taken from the compressed hydrogen stream in line 52 may join a hydrocarbon feed stream in line 32 to provide a hydrocracking feed stream in line 34.

The compressed make-up hydrogen stream in line 26 may also join the compressed hydrogen stream downstream of a split 54, so the make-up hydrogen will be directed to supplying the hydrogen requirements to the hydrocracking reactor 36 or the hydrotreating reactor 92 not filled by the recycle hydrogen stream in line 52. If the compressed make-up hydrogen stream in line 26 joins the compressed hydrogen stream upstream of the split 54, make-up gas is allowed to go to the hydrotreating unit 14 as well as to the hydrocracking unit 12.

The hydrocarbon feed stream is introduced in line 32 perhaps through a surge tank. In one aspect, the process and apparatus described herein are particularly useful for hydroprocessing a hydrocarbonaceous feedstock. Illustrative hydrocarbon feedstocks include hydrocarbonaceous streams having components boiling above about 288° C. (550° F.), such as atmospheric gas oils, VGO, deasphalted, vacuum, and atmospheric residua, coker distillates, straight run distillates, solvent-deasphalted oils, pyrolysis-derived oils, high boiling synthetic oils, cycle oils, hydrocracked feeds, cat cracker distillates and the like. These hydrocarbonaceous feed stocks may contain from about 0.1 to about 4 wt-% sulfur.

A suitable hydrocarbonaceous feedstock is a VGO or other hydrocarbon fraction having at least about 50 percent by weight, and usually at least about 75 percent by weight, of its components boiling at a temperature above about 399° C. (750° F.). A typical VGO normally has a boiling point range between about 315° C. (600° F.) and about 565° C. (1050° F.).

Hydrocracking refers to a process in which hydrocarbons crack in the presence of hydrogen to lower molecular weight hydrocarbons. A hydrocracking reactor 36 is in downstream communication with the one or more compressors 22 on the make-up hydrogen line 20 and the hydrocarbon feed line 32. The hydrocracking feed stream in line 34 may be heat exchanged with a hydrocracking effluent stream in line 38 and further heated in a fired heater before entering the hydrocracking reactor 36 for hydrocracking the hydrocarbon stream to lower boiling hydrocarbons.

The hydrocracking reactor 36 may comprise one or more vessels, multiple beds of catalyst in each vessel, and various combinations of hydrotreating catalyst and hydrocracking catalyst in one or more vessels. In some aspects, the hydrocracking reaction provides total conversion of at least about 20 vol-% and typically greater than about 60 vol-% of the hydrocarbon feed to products boiling below the diesel cut point. The hydrocracking reactor 36 may operate at partial conversion of more than about 50 vol-% or full conversion of at least about 90 vol-% of the feed based on total conversion. To maximize diesel, full conversion is effective. The first vessel or bed may include hydrotreating catalyst for the purpose of demetallizing, desulfurizing or denitrogenating the hydrocracking feed.

The hydrocracking reactor 36 may be operated at mild hydrocracking conditions. Mild hydrocracking conditions will provide about 20 to about 60 vol-%, preferably about 20 to about 50 vol-%, total conversion of the hydrocarbon feed to product boiling below the diesel cut point. In mild hydrocracking, converted products are biased in favor of diesel. In a mild hydrocracking operation, the hydrotreating catalyst has just as much or a greater conversion role than hydrocracking catalyst. Conversion across the hydrotreating catalyst may be a significant portion of the overall conversion. If the hydrocracking reactor 36 is intended for mild hydrocracking, it is contemplated that the mild hydrocracking reactor 36 may be loaded with all hydrotreating catalyst, all hydrocracking catalyst, or some beds of hydrotreating catalyst and beds of hydrocracking catalyst. In the last case, the beds of hydrocracking catalyst may typically follow beds of hydrotreating catalyst. Most typically, three beds of hydrotreating catalyst may be followed by zero, one or two 2 beds of hydrocracking catalyst.

Figure 1:
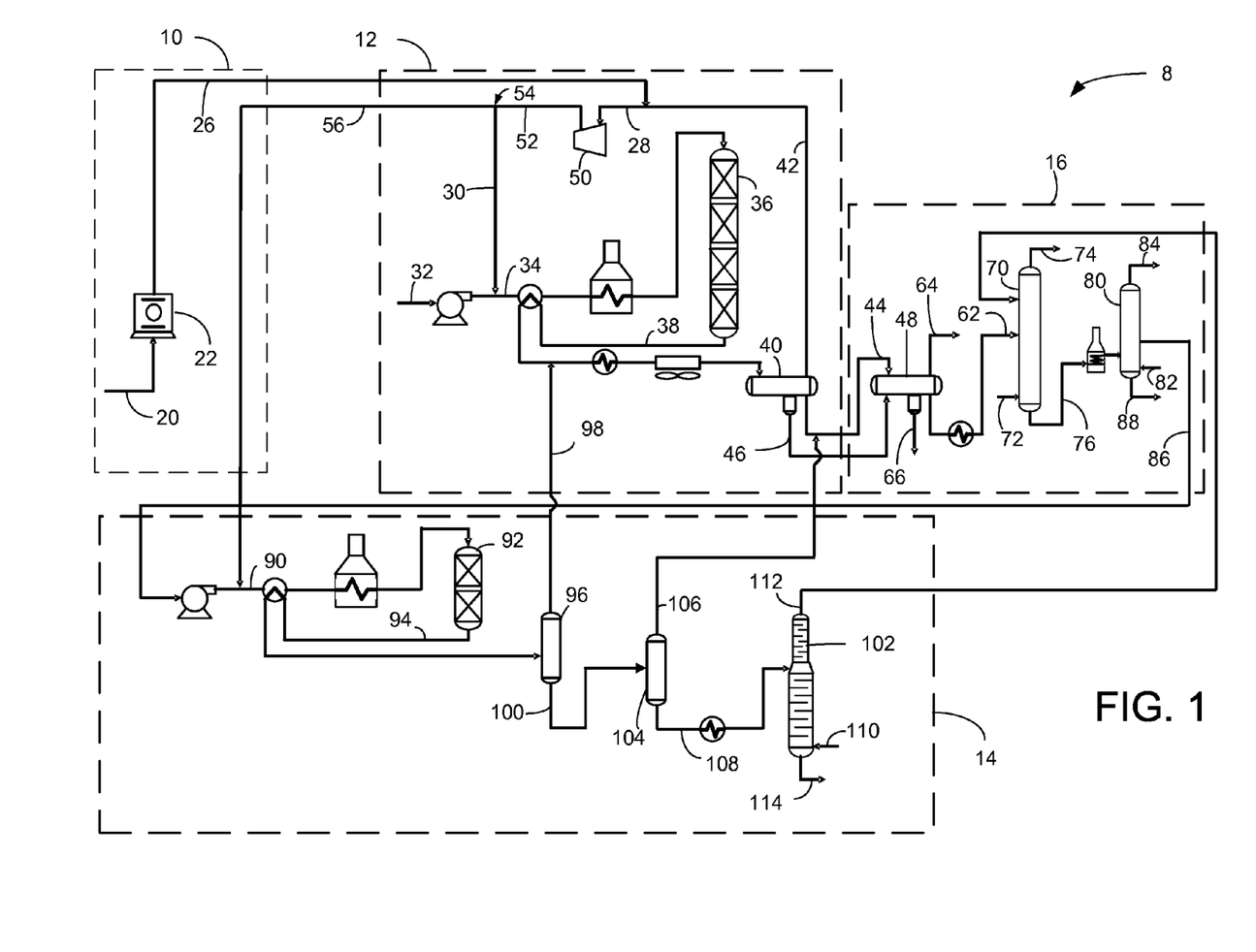
FIG. 1 is a simplified process flow diagram of an embodiment of the present invention.

The hydrocracking reactor 36 in FIG. 1 has four beds in one reactor vessel. If mild hydrocracking is desired, it is contemplated that the first three catalyst beds comprise hydrotreating catalyst and the last catalyst bed comprise hydrocracking catalyst. If partial or full hydrocracking is preferred, additional beds of hydrocracking catalyst may be used than in mild hydrocracking.

At mild hydrocracking conditions, the feed is selectively converted to heavy products such as diesel and kerosene with a low yield of lighter hydrocarbons such as naphtha and gas. Pressure is also moderate to limit the hydrogenation of the bottoms product to an optimal level for downstream processing.

In one aspect, for example, when a balance of middle distillate and gasoline is preferred in the converted product, mild hydrocracking may be performed in the first hydrocracking reactor 36 with hydrocracking catalysts that utilize amorphous silica-alumina bases or low-level zeolite bases combined with one or more Group VIII or Group VIB metal hydrogenating components. In another aspect, when middle distillate is significantly preferred in the converted product over gasoline production, partial or full hydrocracking may be performed in the first hydrocracking reactor 36 with a catalyst which comprises, in general, any crystalline zeolite cracking base upon which is deposited a Group VIII metal hydrogenating component. Additional hydrogenating components may be selected from Group VIB for incorporation with the zeolite base.

The zeolite cracking bases are sometimes referred to in the art as molecular sieves and are usually composed of silica, alumina and one or more exchangeable cations such as sodium, magnesium, calcium, rare earth metals, etc. They are further characterized by crystal pores of relatively uniform diameter between about 4 and about 14 Angstroms ($10^{-10}$ meters). It is preferred to employ zeolites having a relatively high silica/alumina mole ratio between about 3 and about 12. Suitable zeolites found in nature include, for example, mordenite, stilbite, heulandite, ferrierite, dachiardite, chabazite, erionite and faujasite. Suitable synthetic zeolites include, for example, the B, X, Y and L crystal types, e.g., synthetic faujasite and mordenite. The preferred zeolites are those having crystal pore diameters between about 8-12 Angstroms ($10^{-10}$ meters), wherein the silica/alumina mole ratio is about 4 to 6. One example of a zeolite falling in the preferred group is synthetic Y molecular sieve.

The natural occurring zeolites are normally found in a sodium form, an alkaline earth metal form, or mixed forms. The synthetic zeolites are nearly always prepared first in the sodium form. In any case, for use as a cracking base it is preferred that most or all of the original zeolitic monovalent metals be ion-exchanged with a polyvalent metal and/or with an ammonium salt followed by heating to decompose the ammonium ions associated with the zeolite, leaving in their place hydrogen ions and/or exchange sites which have actually been decationized by further removal of water. Hydrogen or "decationized" Y zeolites of this nature are more particularly described in U.S. Pat. No. 3,130,006.

Mixed polyvalent metal-hydrogen zeolites may be prepared by ion-exchanging first with an ammonium salt, then partially back exchanging with a polyvalent metal salt and then calcining. In some cases, as in the case of synthetic mordenite, the hydrogen forms can be prepared by direct acid treatment of the alkali metal zeolites. In one aspect, the preferred cracking bases are those which are at least about 10 percent, and preferably at least about 20 percent, metal-cation-deficient, based on the initial ion-exchange capacity. In another aspect, a desirable and stable class of zeolites is one wherein at least about 20 percent of the ion exchange capacity is satisfied by hydrogen ions.

The active metals employed in the preferred hydrocracking catalysts of the present invention as hydrogenation components are those of Group VIII, i.e., iron, cobalt, nickel, ruthenium, rhodium, palladium, osmium, iridium and platinum. In addition to these metals, other promoters may also be employed in conjunction therewith, including the metals of Group VIB, e.g., molybdenum and tungsten. The amount of hydrogenating metal in the catalyst can vary within wide ranges. Broadly speaking, any amount between about 0.05 percent and about 30 percent by weight may be used. In the case of the noble metals, it is normally preferred to use about 0.05 to about 2 wt-%.

The method for incorporating the hydrogenating metal is to contact the base material with an aqueous solution of a suitable compound of the desired metal wherein the metal is present in a cationic form. Following addition of the selected hydrogenating metal or metals, the resulting catalyst powder is then filtered, dried, pelleted with added lubricants, binders or the like if desired, and calcined in air at temperatures of, e.g., about 371° to about 648° C. (about 700° to about 1200° F.) in order to activate the catalyst and decompose ammonium ions. Alternatively, the base component may first be pelleted, followed by the addition of the hydrogenating component and activation by calcining.

The foregoing catalysts may be employed in undiluted form, or the powdered catalyst may be mixed and copelleted with other relatively less active catalysts, diluents or binders such as alumina, silica gel, silica-alumina cogels, activated clays and the like in proportions ranging between about 5 and about 90 wt-%. These diluents may be employed as such or they may contain a minor proportion of an added hydrogenating metal such as a Group VIB and/or Group VIII metal. Additional metal promoted hydrocracking catalysts may also be utilized in the process of the present invention which comprises, for example, aluminophosphate molecular sieves, crystalline chromosilicates and other crystalline silicates. Crystalline chromosilicates are more fully described in U.S. Pat. No. 4,363,718.

By one approach, the hydrocracking conditions may include a temperature from about 290° C. (550° F.) to about 468° C. (875° F.), preferably 343° C. (650° F.) to about 435° C. (815° F.), a pressure from about 3.5 MPa (500 psig) to about 20.7 MPa (3000 psig), a liquid hourly space velocity (LHSV) from about 1.0 to less than about 2.5 $hr^{-1}$ and a hydrogen rate of about 421 to about 2,527 $Nm^3/m^3$ oil (2,500-15,000 scf/bbl). If mild hydrocracking is desired, conditions may include a temperature from about 315° C. (600° F.) to about 441° C. (825° F.), a pressure from about 5.5 to about 13.8 MPa (gauge) (800 to 2000 psig) or more typically about 6.9 to about 11.0 MPa (gauge) (1000 to 1600 psig), a liquid hourly space velocity (LHSV) from about 0.5 to about 2 $hr^{-1}$ and preferably about 0.7 to about 1.5 $hr^{-1}$ and a hydrogen rate of about 421 to about 1,685 $Nm^3/m^3$ oil (2,500-10,000 scf/bbl).

A hydrocracking effluent exits the hydrocracking reactor 36 in line 38. The hydrocracking effluent in line 38 is heat exchanged with the hydrocracking feed in line 34 and in an embodiment may be cooled before entering a cold separator 40. The cold separator 40 is in downstream communication with the hydrocracking reactor 36. The cold separator may be operated at about 46° to about 63° C. (115° to 145° F.) and just below the pressure of the hydrocracking reactor 36 accounting for pressure drop to keep hydrogen and light gases in the overhead and normally liquid hydrocarbons in the bottoms. The cold separator 40 provides the vaporous hydrocracking effluent stream comprising hydrogen in an cold separator overhead line 42 and a liquid hydrocracking effluent stream in a cold separator bottoms line 44. The cold separator also has a boot for collecting an aqueous phase in line 46. The vaporous hydrocracking effluent stream in the overhead line 42 may be scrubbed with a solution to remove ammonia and hydrogen sulfide as is conventional prior to recycle of the vaporous hydrocracking effluent stream comprising hydrogen to the recycle gas compressor 50.

At least a portion of the hydrocracking effluent stream 38 may be fractionated in a fractionation section 16 in downstream communication with the hydrocracking reactor 36 to produce a diesel stream in line 86. In an aspect, the liquid hydrocracking effluent stream 44 may be fractionated in the fractionation section 16. In a further aspect, the fractionation section 16 may include a cold flash drum 48. The liquid hydrocracking effluent stream 44 may be flashed in the cold flash drum 48 which may be operated at the same temperature as the cold separator 40 but at a lower pressure of between about 1.4 MPa and about 3.1 MPa (gauge) (200-450 psig) to provide a light liquid stream in a bottoms line 62 from the liquid hydrocracking effluent stream and a light ends stream in an overhead line 64. The aqueous stream in line 46 from the boot of the cold separator may also be directed to the cold flash drum 48. A flash aqueous stream is removed from a boot in the cold flash drum 48 in line 66. The light liquid stream in bottoms line 62 may be further fractionated in the fractionation section 16.

The fractionation section 16 may include a stripping column 70 and a fractionation column 80. The light liquid stream in bottoms line 62 may be heated and fed to the stripping column 70. The light liquid stream which is liquid hydrocracking effluent may be stripped with steam from line 72 to provide a light ends stream of hydrogen, hydrogen sulfide, steam and other gases in an overhead line 74. A portion of the light ends stream may be condensed and refluxed to the stripper column 70. The stripping column 70 may be operated with a bottoms temperature between about 232° and about 288° C. (450° to 550° F.) and an overhead pressure of about 690 to about 1034 kPa (gauge) (100 to 150 psig). A hydrocracked bottoms stream in line 76 may be heated in a fired heater and fed to the fractionation column 80.

The fractionation column 80 may also strip the hydrocracked bottoms with steam from line 82 to provide an overhead naphtha stream in line 84, a diesel stream in line 86 from a side cut and an unconverted oil stream in line 88 which may be suitable for further processing, such as in an FCC unit. The overhead naphtha stream in line 84 may require further processing before blending in the gasoline pool. It will usually require catalytic reforming to improve the octane number. The reforming catalyst will often require the overhead naphtha to be further desulfurized in a naphtha hydrotreater prior to reforming. In an aspect, the hydrocracked naphtha may be desulfurized in an integrated hydrotreater 92. It is also contemplated that a further side cut be taken to provide a separate light diesel or kerosene stream taken above a heavy diesel stream taken in line 86. A portion of the overhead naphtha stream in line 84 may be condensed and refluxed to the fractionation column 80. The fractionation column 80 may be operated with a bottoms temperature between about 288° and about 385° C. (550° to 725° F.), preferably between about 315° and about 357° C. (600° to 675° F.) and at or near atmospheric pressure. A portion of the hydrocracked bottoms may be reboiled and returned to the fractionation column 80 instead of using steam stripping.

The diesel stream in line 86 is reduced in sulfur content but may not meet a low sulfur diesel (LSD) specification which is less than 50 wppm sulfur, an ULSD specification which is less than 10 wppm sulfur, or other specifications. Hence, it must be further finished in the diesel hydrotreating unit 14.

The diesel stream in line 86 may be joined by the second hydrotreating hydrogen stream taken from the compressed hydrogen stream in the compressed hydrogen line 52 at the split 54 in a second hydrogen split line 56 to provide a hydrotreating feed stream 90. The diesel stream in line 86 may also be mixed with a co-feed that is not shown. The hydrotreating feed stream 90 may be heat exchanged with the hydrotreating effluent in line 94, further heated in a fired heater and directed to a hydrotreating reactor 92. Consequently, the hydrotreating reactor is in downstream communication with the fractionation section 16, the compressed hydrogen line 52 and the hydrocracking reactor 36. In the hydrotreating reactor 92, the diesel stream is hydrotreated in the presence of a hydrotreating hydrogen stream and hydrotreating catalyst to provide a hydrotreating effluent stream 94. In an aspect, all of the hydrotreating hydrogen stream is provided from the compressed hydrogen stream in line 52 via second hydrogen split line 56.

The hydrotreating reactor 92 may comprise more than one vessel and multiple beds of catalyst. The hydrotreating reactor 92 in FIG. 1 has two beds in one reactor vessel. In the hydrotreating reactor, hydrocarbons with heteroatoms are further demetallized, desulfurized and denitrogenated. The hydrotreating reactor may also contain hydrotreating catalyst that is suited for saturating aromatics, hydrodewaxing and hydroisomerization.

If the hydrocracking reactor 36 is operated as a mild hydrocracking reactor, the hydrocracking reactor may operate to convert up to about 20-60 vol-% of feed boiling above diesel boiling range to product boiling in the diesel boiling range. Consequently, the hydrotreating reactor 92 should have very low conversion and is primarily for desulfurization if integrated with a mild hydrocracking reactor 36 to meet fuel specifications such as qualifying as ULSD.

Hydrotreating is a process wherein hydrogen gas is contacted with hydrocarbon in the presence of suitable catalysts which are primarily active for the removal of heteroatoms, such as sulfur, nitrogen and metals from the hydrocarbon feedstock. In hydrotreating, hydrocarbons with double and triple bonds may be saturated. Aromatics may also be saturated. Some hydrotreating processes are specifically designed to saturate aromatics. Cloud point of the hydrotreated product may also be reduced. Suitable hydrotreating catalysts for use in the present invention are any known conventional hydrotreating catalysts and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. It is within the scope of the present invention that more than one type of hydrotreating catalyst be used in the same hydrotreating reactor 92. The Group VIII metal is typically present in an amount ranging from about 2 to about 20 wt-%, preferably from about 4 to about 12 wt-%. The Group VI metal will typically be present in an amount ranging from about 1 to about 25 wt-%, preferably from about 2 to about 25 wt-%.

Preferred hydrotreating reaction conditions include a temperature from about 290° C. (550° F.) to about 455° C. (850° F.), suitably 316° C. (600° F.) to about 427° C. (800° F.) and preferably 343° C. (650° F.) to about 399° C. (750° F.), a pressure from about 4.1 MPa (600 psig), preferably 6.2 MPa (900 psig) to about 13.1 MPa (1900 psig), a liquid hourly space velocity of the fresh hydrocarbonaceous feedstock from about 0.5 hr$^{-1}$ to about 4 hr$^{-1}$, preferably from about 1.5 to about 3.5 hr$^{-1}$, and a hydrogen rate of about 168 to about 1,011 Nm$^3$/m$^3$ oil (1,000-6,000 scf/bbl), preferably about 168 to about 674 Nm$^3$/m$^3$ oil (1,000-4,000 scf/bbl) for diesel feed, with a hydrotreating catalyst or a combination of hydrotreating catalysts. The hydrotreating unit 14 is integrated with the hydrocracking unit 12, so they both operate at about the same pressure accounting for normal pressure drop.

The hydrotreating effluent stream in line 94 may be heat exchanged with the hydrotreating feed stream in line 90. The hydrotreating effluent stream in line 94 may be separated in a warm separator 96 to provide a vaporous hydrotreating effluent stream comprising hydrogen in a warm separator overhead line 98 and a liquid hydrotreating effluent stream in a warm separator bottoms line 100. The vaporous hydrotreating effluent stream comprising hydrogen may be mixed with the hydrocracking effluent stream in line 38 perhaps prior to cooling and enter into the cold separator 40. The warm separator 96 may be operated between about 149° and about 260° C. (300° to 500° F.). The pressure of the warm separator 96 is just below the pressure of the hydrotreating reactor 96 accounting for pressure drop. The warm separator may be operated to obtain at least 90 wt-% diesel and preferably at least 93 wt-% diesel in the liquid stream in line 100. All of the other hydrocarbons and gases go up in the vaporous hydrotreating effluent stream in line 98 which joins the hydrocracking effluent in line 38 and may be processed after heating therewith first by entering the cold separator 40. Consequently, the cold separator 40 and, thereby, the recycle gas compressor 50 are in downstream communication with the warm separator overhead line 98. Accordingly, recycle gas loops from both the hydrocracking section 12 and the hydrotreating section 14 share the same recycle gas compressor 50. Moreover, at least a portion of the hydrotreating effluent stream in hydrotreating effluent line 94 provided in the warm separator overhead stream comprising hydrogen and hydrocarbons lighter than diesel in the warm separator overhead line 98 is mixed with at least a portion of the hydrocracking effluent stream in hydrocracking effluent line 38.

The liquid hydrotreating effluent stream in line 100 may be fractionated in a hydrotreating stripper column 102. In an aspect, fractionation of the liquid hydrotreating effluent stream in line 100 may include flashing it in a warm flash drum 104 which may be operated at the same temperature as the warm separator 96 but at a lower pressure of between about 1.4 MPa and about 3.1 MPa (gauge) (200-450 psig). A warm flash overhead stream in the warm flash overhead line 106 may be joined to the liquid hydrocracking effluent stream in the cold separator bottoms line 44 for further fractionation therewith. Consequently, at least a portion of the hydrotreating effluent stream in line 94 comprising hydrogen provided in the warm flash overhead stream in the warm flash overhead line 106 is mixed with at least a portion of the hydrocracking effluent stream in line 38 provided in the liquid hydrocracking effluent stream in the cold separator bottoms line 44.

The warm flash bottoms stream in line 108 may be heated and fed to the stripper column 102. The warm flash bottoms may be stripped in the stripper column 102 with steam from line 110 to provide a naphtha and light ends stream in overhead line 112. The naphtha and light ends stream in line 112 may be fed to the fractionation section 16 and specifically to the stripping column 70 at an elevation above the feed point of light liquid stream in line 62. A product diesel stream is recovered in bottoms line 114 comprising less than 50 wppm sulfur qualifying it as LSD and preferably less than 10 wppm sulfur qualifying it as ULSD. It is contemplated that the stripper column 102 may be operated as a fractionation column with a reboiler instead of with stripping steam.

By operating the warm separator 96 at elevated temperature to reject most hydrocarbons lighter than diesel, the hydrotreating stripping column 102 may be operated more simply because it is not relied upon to separate naphtha from lighter components and because there is very little naphtha to separate from the diesel. Moreover, the warm separator 96 makes sharing of a cold separator 40 with the hydrocracking reactor 36 possible and heat useful for fractionation in the stripper column 102 is retained in the hydrotreating liquid effluent.

Figure 2:
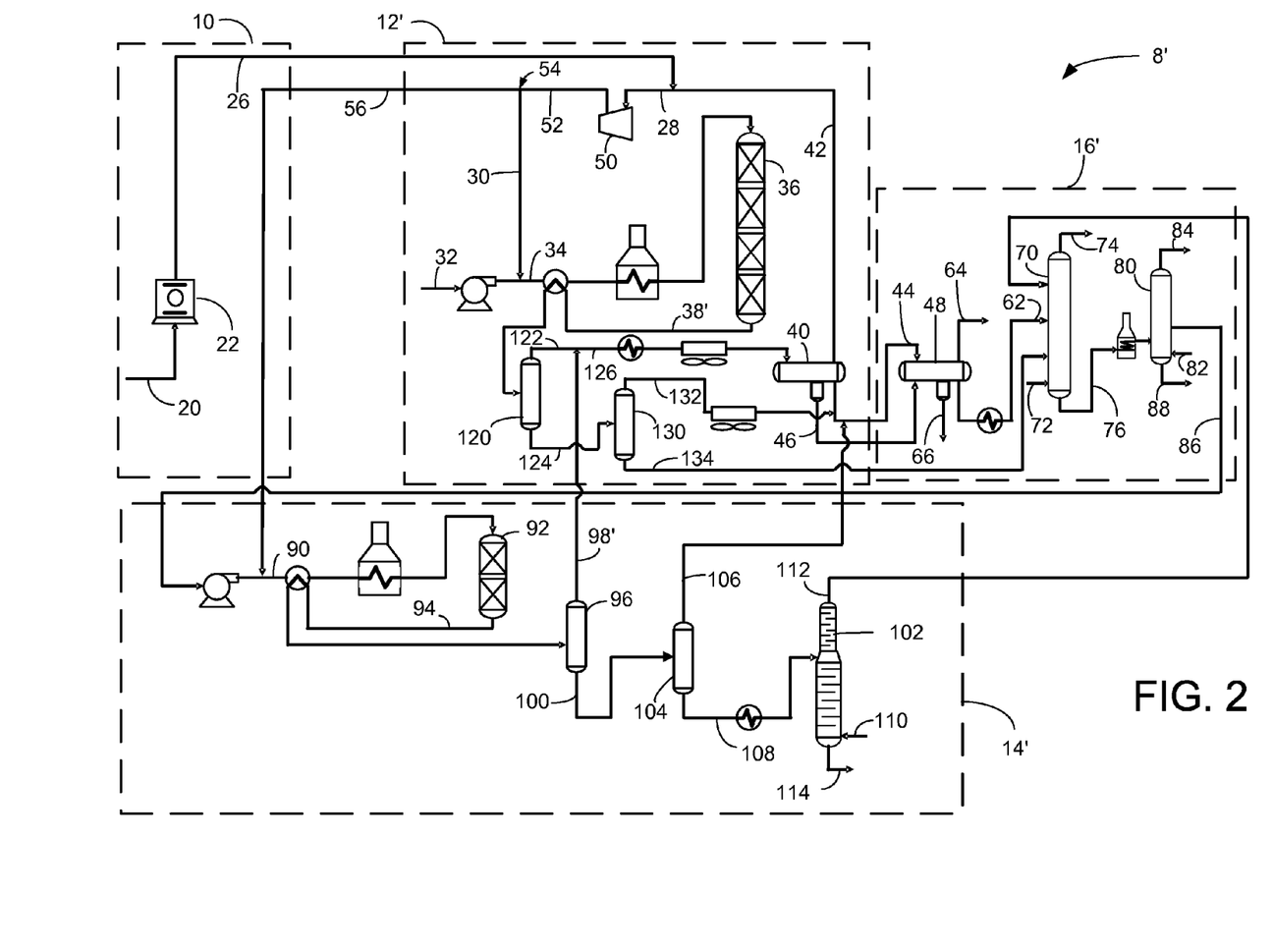
FIG. 2 is a simplified process flow diagram of an alternative embodiment of the present invention.

FIG. 2 illustrates an embodiment of a process and apparatus 8' that utilizes a hot separator 120 to initially separate the hydrocracking effluent in line 38'. Many of the elements in FIG. 2 have the same configuration as in FIG. 1 and bear the same reference number. Elements in FIG. 2 that correspond to elements in FIG. 1 but have a different configuration bear the same reference numeral as in FIG. 1 but are marked with a prime symbol (').

The hot separator 120 in the hydrocracking section 12' is in downstream communication with the hydrocracking reactor 36 and provides a vaporous hydrocarbonaceous stream in an overhead line 122 and a liquid hydrocarbonaceous stream in a bottoms line 124. The hot separator 120 operates at about 177° to about 343° C. (350° to 650° F.) and preferably operates at about 232° to about 288° C. (450° to 550° F.). The hot separator may be operated at a slightly lower pressure than the hydrocracking reactor 36 accounting for pressure drop. The vaporous hydrocarbonaceous stream in line 122 may be joined by the vaporous hydrotreating effluent stream in line 98' from the hydrotreating section 14' and be mixed and transported together in line 126. The mixed stream in line 126 may be cooled before entering the cold separator 40. Consequently, the vaporous hydrocracking effluent may be separated along with the vaporous hydrotreating effluent stream in the cold separator 40 to provide the vaporous hydrocracking effluent comprising hydrogen in line 42 and the liquid hydrocracking effluent in line 44 and which are processed as previously described with respect to FIG. 1. The cold separator 40, therefore, is in downstream communication with the overhead line 122 of the hot separator 120 and an overhead line 98' of the warm separator 96.

The liquid hydrocarbonaceous stream in bottoms line 124 may be fractionated in the fractionation section 16'. In an aspect, the liquid hydrocarbonaceous stream in line 124 may be flashed in a hot flash drum 130 to provide a light ends stream in an overhead line 132 and a heavy liquid stream in a bottoms line 134. The hot flash drum 130 may be operated at the same temperature as the hot separator 120 but at a lower pressure of between about 1.4 MPa and about 3.1 MPa (gauge) (200 to 450 psig). The heavy liquid stream in bottoms line 134 may be further fractionated in the fractionation section 16'. In an aspect, the heavy liquid stream in line 134 may be introduced into the stripping column 70 at a lower elevation than the feed point light liquid stream in line 62.

The rest of the embodiment in FIG. 2 may be the same as described for FIG. 1 with the previous noted exceptions.

Preferred embodiments of this invention are described herein, including the best mode known to the inventors for carrying out the invention. It should be understood that the illustrated embodiments are exemplary only, and should not be taken as limiting the scope of the invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated. Pressures are given at the vessel outlet and particularly at the vapor outlet in vessels with multiple outlets.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing diesel from a hydrocarbon stream comprising:
   compressing a make-up hydrogen stream in a compressor to provide a compressed make-up hydrogen stream;
   taking a hydrocracking hydrogen stream from the compressed make-up hydrogen stream;
   hydrocracking the hydrocarbon stream in the presence of the hydrocracking hydrogen stream and hydrocracking catalyst to provide a hydrocracking effluent stream;
   separating the hydrocracking effluent stream into a vaporous hydrocracking effluent stream comprising hydrogen and a liquid hydrocracking effluent stream;
   compressing the vaporous hydrocracking effluent stream to provide a compressed hydrogen stream;
   taking a hydrotreating hydrogen stream from the compressed hydrogen stream;
   fractionating the liquid hydrocracking effluent stream to provide a diesel stream;
   hydrotreating the diesel stream in the presence of a hydrotreating hydrogen stream and hydrotreating catalyst to provide a hydrotreating effluent stream; and
   separating the hydrotreating effluent stream into a vaporous hydrotreating effluent stream comprising hydrogen and a liquid hydrotreating effluent stream comprising at least 90 wt-% diesel and mixing the vaporous hydrotreating effluent stream comprising hydrogen with the hydrocracking effluent stream.

2. The process of claim 1 wherein all of the hydrotreating hydrogen stream is provided from the compressed hydrogen stream.

3. The process of claim 1 further comprising flashing a light liquid stream from the liquid hydrocracking effluent stream and further fractionating the light liquid stream.

4. The process of claim 1 further comprising separating the hydrocracking effluent into a vaporous hydrocarbonaceous stream and a liquid hydrocarbonaceous stream and further separating the vaporous hydrocarbonaceous stream to provide the vaporous hydrocracking effluent stream comprising hydrogen and the liquid hydrocracking effluent stream.

5. The process of claim 4 further comprising fractionating the liquid hydrocarbonaceous stream to provide the diesel stream.

6. The process of claim 5 further comprising flashing a heavy liquid stream from the liquid hydrocarbonaceous stream and further fractionating the heavy liquid stream.

7. The process of claim 1 further comprising fractionating the liquid hydrotreating effluent stream comprising at least 90 wt-% diesel to provide an ultra low sulfur diesel stream.

8. The process of claim 1 further comprising fractionating the hydrotreating effluent stream to provide an ultra low sulfur diesel stream.

9. The process of claim 1 further comprising:
   compressing said compressed make-up hydrogen stream in a recycle gas compressor to provide a compressed hydrogen stream; and
   mixing at least a portion of the hydrotreating effluent stream comprising hydrogen with at least a portion of the hydrocracking effluent stream.

10. The process of claim 9 further comprising separating the hydrotreating effluent stream into a vaporous hydrotreating effluent stream comprising hydrogen and a liquid hydrotreating effluent stream and fractionating the liquid hydrotreating effluent stream comprising at least 90 wt-% diesel to provide an ultra low sulfur diesel stream.

11. The process of claim 9 further comprising separating the hydrocracking effluent stream into a vaporous hydrocracking effluent stream comprising hydrogen and a liquid hydrocracking effluent stream; compressing the vaporous hydrocracking effluent stream with the compressed make-up hydrogen stream to provide the compressed hydrogen stream and taking all of the hydrotreating hydrogen stream from the compressed hydrogen stream.

12. The process of claim 1 wherein taking said hydrocracking hydrogen stream from the compressed make-up hydrogen stream comprises:
   compressing said compressed make-up hydrogen stream in a recycle gas compressor to provide a compressed hydrogen stream; and
   taking a hydrocracking hydrogen stream from the compressed hydrogen stream.

* * * * *